(12) United States Patent
Whinnett et al.

(10) Patent No.: US 9,399,138 B2
(45) Date of Patent: Jul. 26, 2016

(54) APPARATUS AND METHOD FOR PROGRAMMING A PACEMAKER

(75) Inventors: Zachary Whinnett, London (GB); Darrel Francis, Harrow (GB)

(73) Assignee: Imperial Innovations Limited (GB)

( * ) Notice: Subject to any disclaimer, the term of this patent is extended or adjusted under 35 U.S.C. 154(b) by 1035 days.

(21) Appl. No.: 12/297,988

(22) PCT Filed: Apr. 20, 2007

(86) PCT No.: PCT/GB2007/001446
§ 371 (c)(1),
(2), (4) Date: Oct. 13, 2009

(87) PCT Pub. No.: WO2007/125280
PCT Pub. Date: Nov. 8, 2007

(65) Prior Publication Data
US 2010/0030295 A1    Feb. 4, 2010

(30) Foreign Application Priority Data

Apr. 21, 2006  (GB) .................................. 0607938.8

(51) Int. Cl.
*A61N 1/00* (2006.01)
*A61N 1/362* (2006.01)
*A61N 1/365* (2006.01)
(Continued)

(52) U.S. Cl.
CPC .............. *A61N 1/3627* (2013.01); *A61N 1/3682* (2013.01); *A61N 1/3688* (2013.01); *A61N 1/36564* (2013.01); *A61N 1/37235* (2013.01); *A61N 1/37264* (2013.01)

(58) Field of Classification Search
CPC ............ A61N 1/3627; A61N 1/36564; A61N 1/3682; A61N 1/3688; A61N 1/37235; A61N 1/37264
USPC ........... 607/2–4, 9–20, 23, 25, 27, 28, 30, 62, 607/119–132
See application file for complete search history.

(56) References Cited

U.S. PATENT DOCUMENTS 6,925,326 B1 * 8/2005 Levine et al. ................. 600/510
7,546,161 B1 * 6/2009 Bjorling et al. ................ 607/28
(Continued)

FOREIGN PATENT DOCUMENTS

EP   1 321 167 A2   6/2003
WO   2006/008535 A1   1/2006

OTHER PUBLICATIONS

Cha, et al., "Difference in Mechanical Atrioventricular Delay Between Atrial Sensing and Atrial Pacing . . . ", "Journal of Interventional Cardiac Electrophysiology", Jun. 2002, pp. 133-140, vol. 6, No. 2, XP002445291, Published in: NE.
(Continued)

*Primary Examiner* — Niketa Patel
*Assistant Examiner* — Lindsey G Hankins
(74) *Attorney, Agent, or Firm* — Kaplan Breyer Schwarz & Ottesen LLP (57) ABSTRACT

A pacemaker programming apparatus for programming a pacemaker in an individual. The apparatus comprises means for determining the sensed-paced difference of the pacemaker in the individual: first testing means for determining the optimum AV delay while the pacemaker is atrially pacing at a raised at a heart rate; and calculation means for calculating the optimum AV delay determined by the first testing means minus the sensed-paced difference.

38 Claims, 6 Drawing Sheets

(51) Int. Cl.
    *A61N 1/368*    (2006.01)
    *A61N 1/372*    (2006.01)

(56)         References Cited

U.S. PATENT DOCUMENTS

2003/0130702 A1*  7/2003  Kramer et al. .................... 607/9
2004/0172081 A1    9/2004  Wang

OTHER PUBLICATIONS

Dorothee Muelhausen, "International Application No. PCT/GB2007/001446 International Preliminary Report on Patentability", Oct. 22, 2008, Publisher: PCT.

International Search Report, PCT/GB2007/001446, Aug. 17, 2007, Officer: Kris Loveniers.

"Related Indian Patent Application No. IN 2338/MUMNP/2008", "First Examination Report", Jan. 15, 2015, Publisher: India Patent Office, Published in: IN.

* cited by examiner

APPARATUS AND METHOD FOR PROGRAMMING A PACEMAKER

FIELD OF THE INVENTION

The present invention relates to a pacemaker programming apparatus and a computer program therefor. The invention also relates to a method of determining the sensed-paced difference in an individual fitted with a pacemaker; a method of determining the AV delay for a pacemaker; and a method of programming a pacemaker.

BACKGROUND OF THE INVENTION

It is known to fit pacemakers to patients suffering from chronic heart failure where the walls of the ventricles (the main pumping chambers of the human heart) are no longer synchronised. Such pacemakers are known as biventricular (or resynchronising) pacemakers and can be used to effect cardiac resynchronisation therapy (CRT). A biventricular pacemaker stimulates both the left and right sides of the heart in order to shorten atrioventricular delay and improve synchrony of ventricular contractions but does not necessarily vary the heart rate per se. The fitting of a biventricular pacemaker to an appropriate patient has been observed to result in a prompt improvement in haemodynamic status, with an increase in peak rise in intraventricular pressure, an increase in stroke volume and consequently higher systemic arterial blood pressure.

In principle, there are, in fact, two classes of biventricular pacemaker. An atriobiventricular pacemaker has the following three basic attributes, whose settings may be adjusted.

1) The heart rate. In many patients with resynchronizing pacemakers, the patient's natural heart rate is satisfactory, and the pacemaker is programmed merely to follow the natural heart rate. In other patients, the natural heart rate is too low, and the pacemaker is programmed to pace at a higher rate. In both groups of patients, the pacemaker may change between following the natural heart rate and actively controlling the heart rate, for example when the patient undertakes physical exertion.

2) The atrioventricular ("AV") delay. This is the time interval between the atrium and the ventricles getting electrical stimulation. This delay is often set at about 120 ms when the pacemaker is initially implanted.

3) The left ventricle versus right ventricle ("LV-RV" or simply "VV") delay. This is the time interval between the left ventricle and the right ventricle getting electrical stimulation. It is often set at 0 ms when the pacemaker is manufactured. Some manufacturers have a small non-zero lower limit, such as 4 ms, which can be treated as 0 ms for practical purposes.

The other class of biventricular pacemaker has two ventricular leads but, unlike the atrioventricular pacemaker, only the setting of VV delay can be adjusted and not the setting of AV delay.

In order to provide the optimum settings for these attributes, and especially atrioventricular (AV) delay, in a particular patient, many centres use an echocardiographic approach to selecting pacemaker programming. The most commonly used method is to determine, at resting heart rate, the longest filling time associated with complete atrial systole uninterrupted by ventricular systole. However, one problem with this approach is that there is little data to suggest that this approach optimizes hemodynamics in patients with chronic heart failure who have resynchronizing pacemakers.

It has been observed that blood pressure rises with the onset of biventricular pacing, and therefore it is theoretically possible to optimize the activity of a biventricular pacemaker by adjusting the attributes of the pacemaker while measuring the blood pressure of the patient. The problem with using a regular sphygmomanometer with an arm band cuff in order to measure blood pressure in these situations would be that taking each blood pressure measurement requires a considerable amount of time and, in practice, many different measurements would have to be taken during the optimisation process. Thus optimization by this method is entirely impractical.

It has also been proposed to determine blood pressure while optimizing biventricular pacemaker attributes by invasive haemodynamic monitoring of the blood pressure of the patient. However, the problem with this approach is that the clinical intricacy involved and the non-trivial risk associated with invasive blood pressure monitoring make it unsuitable for routine optimization of pacemaker attribute settings in normal practice.

WO2006/008535 discloses a method of optimising pacemaker settings by using non-invasive means, such as a finapres, to determine the blood pressure of the patient fitted with the pacemaker. WO2006/008535 also discloses that it is preferable to determine the optimum settings of a pacemaker while the patient has a raised heart rate. This is because patients with heart failure usually become symptomatic during exercise.

One problem with such prior art approaches to optimizing the settings of pacemaker attributes is that they require the heart rate to be raised by a patient exercising during the optimization process. Optimization during exercise has proven to be technically difficult using the currently available methods. Invasive haemodynamics are not suitable because of their invasive nature and echocardiographic techniques have limited use because of the practical limitation of acquiring images during exercise. Even if non-invasive means, such as a finapres, are used to determine haemodynamics, problems still occur for patients who are unable to exercise in order to raise their heart rate. Problems also occur at centres where the facilities are not available for exercise optimisation.

BRIEF SUMMARY OF THE INVENTION

The present invention seeks to alleviate the above problems, particularly as regards the optimization of AV delay in patients fitted with pacemakers.

According to one aspect of the present invention there is provided a pacemaker programming apparatus for programming a pacemaker in an individual comprising:
  means for determining the sensed-paced difference of the pacemaker in the individual;
  first testing means for determining the optimum AV delay while the pacemaker is atrially pacing at a raised heart rate; and
  calculation means for calculating the optimum AV delay determined by the first testing means minus the sensed-paced difference.

Conveniently, the means for determining the sensed-paced difference of the pacemaker comprises:
  second testing means for determining the optimum AV delay while the pacemaker is P-synchronous pacing at a specific heart rate; and
  third testing means for determining the optimum AV delay while a pacemaker is atrially pacing at or near the specific heart rate, the calculation means calculating the sensed-paced difference by deducting the optimum AV delay determined by the second testing means from the optimum AV delay determined by the third testing means.

Preferably, the pacemaker programming apparatus further comprises means to communicate with the pacemaker in the individual.

According to another aspect of the present invention there is provided a computer program for a pacemaker programming apparatus comprising;

an analysis module for determining the sensed-paced difference of a pacemaker in an individual;

a first testing module for determining the optimum AV delay while a pacemaker is atrially pacing at a raised heart rate; and a calculation module for calculating the optimum AV delay determined by the first testing module minus the sensed-paced difference.

Advantageously, the analysis module comprises:

a second testing module for determining the optimum AV delay while a pacemaker is P-synchronous pacing at a specific heart rate; and a third testing module for determining the optimum AV delay while a pacemaker is atrially pacing at or near the specific heart rate;

and wherein the calculation module calculates the sensed-paced difference by deducting the optimum AV delay determined by the second testing module from the optimum AV delay determined by the third testing module.

According to another aspect of the present invention there is provided a method of determining the sensed-paced difference in an individual fitted with a pacemaker comprising the steps of:

i) determining the optimum AV delay while the pacemaker is P-synchronous pacing at a specific heart rate;

ii) determining the optimum AV delay while the pacemaker is atrially pacing at or near the specific heart rate; and iii) determining the difference between the optimum AV delay determined at step i) and the optimum AV delay determined at step ii).

According to a further aspect of the present invention there is provided a method of determining a preferred AV delay for a pacemaker in an individual comprising the steps of:

i) determining the sensed-paced difference of the pacemaker in the individual;

ii) determining the optimum AV delay while the pacemaker is atrially pacing at a raised heart rate; and iii) adjusting the optimum AV delay determined at step ii) with the sensed-paced difference determined at step i).

Conveniently, the raised heart rate is between 90 and 200 bpm, preferably between 95 and 110 bpm.

Preferably, in the method of determining a preferred AV delay for a pacemaker in an individual step i) comprises the method of determining the sensed-paced difference in an individual as described above and step iii) comprises calculating the optimum AV delay determined at a raised heart rate minus the optimum AV delay determined while atrially pacing at or near the specific heart rate plus the optimum AV delay determined while P-synchronous pacing at the specific heart rate.

Advantageously, the method of programming a pacemaker in an individual further comprises the step of:

iv) programming the pacemaker with the AV delay determined at step iii).

Conveniently, the optimum AV delay of a pacemaker is the AV delay which provides the highest blood pressure in an individual.

Preferably, determining the optimum AV delay comprises varying the AV delay whilst measuring the blood pressure of the individual and determining the AV delay which results in the highest blood pressure of the individual.

Advantageously, the optimum AV delay is determined by alternating the AV delay of the pacemaker between a reference AV delay and a range of test AV delays to determine the test AV delay which provides the maximum relative increase in blood pressure in the individual.

Conveniently, the specific heart rate is a rest heart rate.

Preferably, the rest heart rate is between 60 and 100 bpm, more preferably between 65 and 80 bpm.

Advantageously, a heart rate near the specific heart rate is within 10, 15 or 20 bpm of the specific heart rate, preferably within 5 bpm of the specific heart rate.

Conveniently, in the method of determining the sensed-paced difference in an individual step iii) comprises deducting the optimum AV delay determined at step i) from the optimum AV delay determined at step ii).

It is preferred that the pacemaker programming apparatus further comprises a processor programmed with the computer program of the invention.

In this specification, the "sensed-paced difference" of a pacemaker in an individual means the difference in programmed AV delay that is required between P-synchronous pacing and atrioventricular sequential pacing (i.e. "atrial" pacing) in order to achieve the same mechanical left sided AV delay (delay between contraction of the left atrium and left ventricle) at a given heart rate in a particular individual. In one embodiment this is achieved by determining the difference in AV delay required to achieve the highest blood pressure in the individual by P-synchronous pacing compared with atrial pacing.

BRIEF DESCRIPTION OF THE DRAWINGS

In order that the present invention may be better understood and so that further features thereof may be more fully appreciated, embodiments of the invention will now be described with reference to the accompanying figures in which.

DETAILED DESCRIPTION OF THE INVENTION

Figure 1:
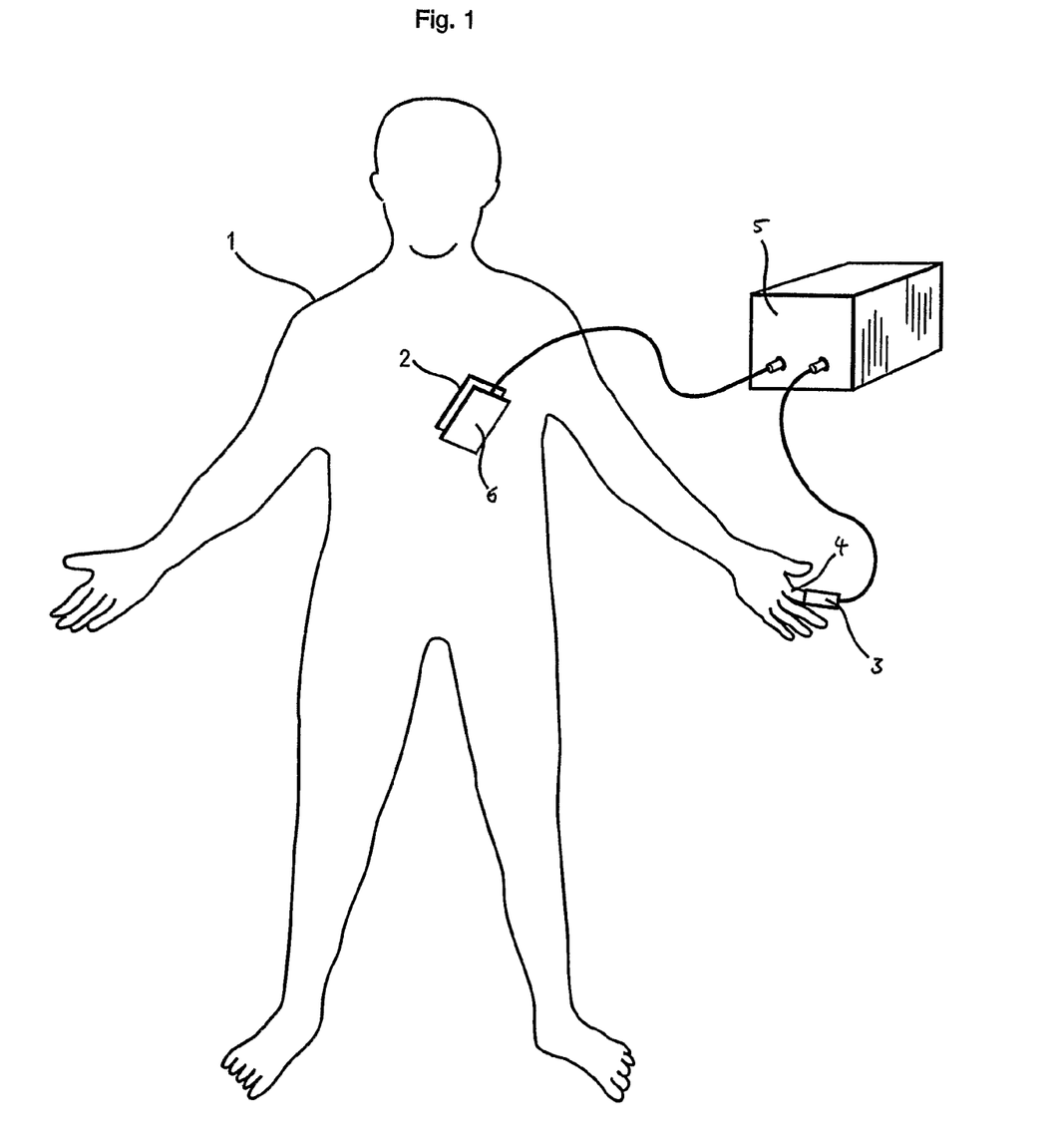
FIG. 1 is a schematic view of a pacemaker programming apparatus in accordance with one embodiment of the present invention.

Referring to FIG. 1, an embodiment of the present invention will now be described. A patient 1 is fitted with a biventricular pacemaker 2. In order to optimise the setting of the AV delay of the pacemaker 2, a finapres 3 is fitted to the index finger 4 of the patient, which is, in turn, connected to a processor 5. The processor is programmed to calculate the blood pressure of the individual from the input from the finapres 3.

The processor 5 is also connected to a transmitter 6 which is located outside of the body of the patient 1, but adjacent to the implanted pacemaker 2 such that the transmitter is in communication with the pacemaker 2.

The processor 5 is programmed to adjust the AV delay of the pacemaker 2 and to assess the blood pressure of the patient at each setting of the AV delay from the input received from the finapres 3.

It is to be appreciated that the biventricular pacemaker 2 can pace the heart of the patient 1 in two different ways: P-synchronous pacing and atrioventricular sequential pacing. In P-synchronous pacing, the atrium of the patient activates itself. This activation is detected by the pacemaker 2 and, after a short delay, the ventricle is then paced. There is a delay between the atrium activation being detected and the ventricle being paced.

In atrioventricular sequential pacing, instead of the atrium activating itself, the atrium is paced by the pacemaker.

Accordingly, atrioventricular sequential pacing can be used to increase the heart rate of an individual to a rate (such as 100 bpm) usually achieved during exercise. Thus atrioventricular sequential pacing can be used to simulate the activity of the heart during exercise. It has been found by the present inventors that the AV delay of a pacemaker is best optimised for the circumstances that exist when the patient is exercising. However, when a patient is naturally exercising, the pacemaker will be engaged in P-synchronous pacing of the heart of the patient. Therefore, in order to provide an accurate model of the patient during real exercise, when optimisation is carried out during simulated exercise, the model must take into account the differences in pacing between P-synchronous pacing (sensed) and atrioventricular sequential pacing (paced) AV delay. This "sensed-paced" difference varies from patient to patient and thus it is necessary to determine the sensed-paced difference in each patient.

In particular, it is important to note that when the AV delay is programmed on the pacemaker this represents the right sided AV delay. It is, however, the mechanical contraction delay between the left atrium and left ventricle which has the predominant effect on systemic haemodynamics[1,2,3]

There are three principle differences between P-synchronous pacing and atrioventricular sequential pacing which need to be taken into account, the atrial sensing delay, atrial pacing latency and differences in intra-atrial delay.

Atrial Sensing Delay

During P-synchronous pacing the programmed right sided AV delay is shorter than the actual right sided AV delay. This is because the pacemaker only detects the onset of atrial depolarization once the amplitude of the depolarization reaches a certain size. This results in a time lag in the detection of the onset of atrial depolarisation; the atrial sensing delay (FIG. 2*a*).

Atrial Pacing Latency

Figure 2:
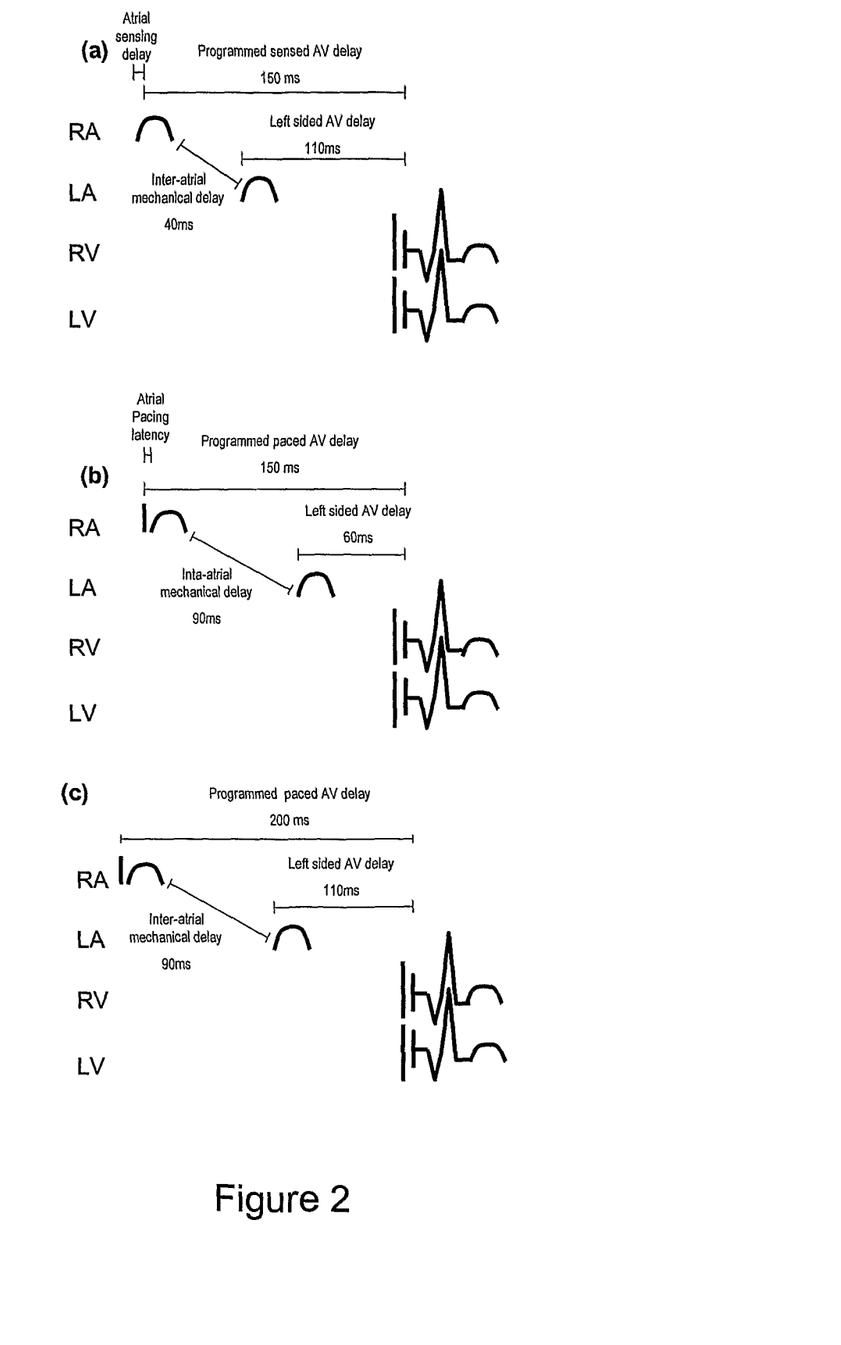
FIG. 2 is a graph showing the variation in time available for the left sided AV delay depending on whether the AV delay is programmed p-wave synchronous or the atrium is paced.

When pacing from the right atrium there is a delay from the time of delivery of the pacing stimulus to the onset of atrial depolarisation, the so called atrial pacing latency.[4] This means that the actual right sided AV delay is slightly shorter than the programmed AV delay (FIG. 2*b*).

Intra-Atrial Delay

The time taken for activation of the left atrium differs depending on whether activation is initiated by intrinsic atrial activity or atrial pacing. Typically the intra-atrial delay is longer for an atrial paced beat compared with intrinsic activation. This delay is likely to be due to less efficient intra-atrial conduction. The difference in intra-atrial delay between paced and sensed activation appears to be patient specific[1,2,3] which is likely to reflect differences in underlying conduction, lead position, atrial size and function. Intra-atrial conduction time appears remains relatively constant when heart rate is altered.[5]

In summary, the cardiac output and systemic haemodynamic effect of AV delay optimisation is ultimately dependent on the left atrial to left ventricular interval. However, it is the right sided AV delay which is programmed through the pacemaker. For P-synchronous pacing (sensed AV delay) the actual right sided AV delay is slightly longer than the delay which is programmed because of the time taken for the pacemaker to sense the onset of atrial depolarisation (atrial sensing delay). As shown in FIG. 2*a*, when pacing the right atrium the actual right sided AV delay is shorter than the programmed AV delay because there is a short latency until the onset of atrial depolarisation. In addition to these differences the time available for the left sided AV delay, is reduced during atrial pacing compared with P-synchronous pacing because there tends to be a prolonged interatrial conduction time with atrial pacing as is shown in FIG. 2*b*. Therefore in order to achieve the same left sided AV delay a longer paced AV delay needs to be programmed as is shown in FIG. 2*c*.

Therefore, in use, after a patient 1 has been fitted with a pacemaker 2, the patient 1 undergoes a process of optimisation of the setting of the AV delay of the pacemaker 2. In order to do this, the blood pressure of the patient is non-invasively monitored by the fitting of the finapres 3, which is connected to the processor 5. The processor 5, is, in turn, a communication with the pacemaker 2, via the transmitter 6.

The first step is to determine the sensed-paced difference of the patient 1. At a resting heart rate (typically in the region of 65 to 80 bpm) the pacemaker 2 is set by the processor 5 to P-synchronous pacing. The AV delay of the pacemaker 2 is then adjusted by the processor 5 while the blood pressure of the patient 1 is monitored via the finapres 3.

For example, in one particularly preferred embodiment, the processor 5 sets the pacemaker 2 to a reference setting of the AV delay for a test period lasting a predetermined number of heartbeats (e.g. 10 heartbeats) during which time the blood pressure of the patient is measured. After the test period, the setting of the AV delay is changed to a first test setting and the blood pressure of the patient 1 is measured for a second test period. The pacemaker is then returned to the reference setting for a third testing period during which time the blood pressure of the patient is determined. Subsequently, the AV delay of the pacemaker is adjusted to a second test setting for another test period during which time the blood pressure of the patient 1 is measured. This process is repeated, with the setting of the AV delay of the pacemaker 2 alternating between the reference setting and a range of test settings. For example, the reference setting may represent an AV delay of 120 ms and the test settings range from 40 to 240 ms in steps of 40 ms. By using this method, each test setting can be compared with the blood pressure at the immediately preceding and immediately subsequent reference setting, thus revealing the change in blood pressure achieved or, in other words, the "relative benefit". This eliminates the effect of any gradual trends in blood pressure. The AV delay which results in the greatest relative increase in blood pressure is thus the optimum AV delay. Further discussion of the measuring of the optimum AV delay is disclosed in WO2006/008535 which is hereby incorporated by reference.

Once the optimum AV delay for the patient during P-synchronous pacing has been determined, the processor switches the pacemaker 2 to atrial pacing and repeats the process of optimising the AV delay for the patient. This optimisation process is also carried out at a resting heart rate. However, in practice, the resting heart rate of a patient undergoing atrial pacing must be slightly higher (e.g. 5 to 10 bpm) than the natural resting heart rate of the patient 1 undergoing P-synchronous pacing. This is because the atrial pacing might otherwise interfere with the naturally occurring pacing of the heart which could result in the inhibition of activity rather than activation of pacing.

Once the optimum AV delay for the patient has been determined during atrial pacing, the sensed-paced difference is calculated by determining the difference between the optimum AV delay determined during P-synchronous pacing and the optimum AV delay determined during atrial pacing. More specifically, the optimum AV delay determined during P-synchronous pacing is deducted from the optimum AV delay determined during atrial pacing.

The next step is to determine the optimum AV delay of the patient during exercise. The processor 5 adjusts the pacemaker 2 (which continues atrially pacing) to increase the heart rate of the patient 1 to a raised heart rate (e.g. 100 to 110 bpm) in order to simulate the patient exercising. The processor 5 then determines the optimum AV delay of the patient 1 at the raised heart rate, in the same way as has been described previously.

The predicted optimum AV delay for the pacemaker is then calculated by calculating the optimum AV delay determined during an atrial pacing at a raised heart rate minus the optimum AV delay determined at a rest heart rate during atrial pacing, plus the optimum AV delay determined during P-synchronous pacing at rest heart rate. In this way, the optimum AV delay determined during simulated exercise is modified to take account of the sensed paced difference of the patient 1.

Finally, the processor 5 adjusts the pacemaker 2 to the optimum AV delay that has been predicted for P-synchronous pacing during exercise.

In the above-described embodiments, the processor 5 is external of the patient 1. However, in alternative embodiments, the processor 5 is incorporated within the implanted pacemaker 2. In these embodiments, during the AV delay optimisation process, the blood pressure of the patient 1 is monitored using a finapres 3 and the signal produced by the finapres 3 is communicated to the processor 5 within the patient 1 via the transmitter 6.

EXAMPLES

Example 1

This is a hypothetical example that illustrates why the paced AV optimum is longer than the sensed AV optimum. The left sided AV delay has the predominant effect on cardiac output and systemic hemodynamics.

Figure 3:
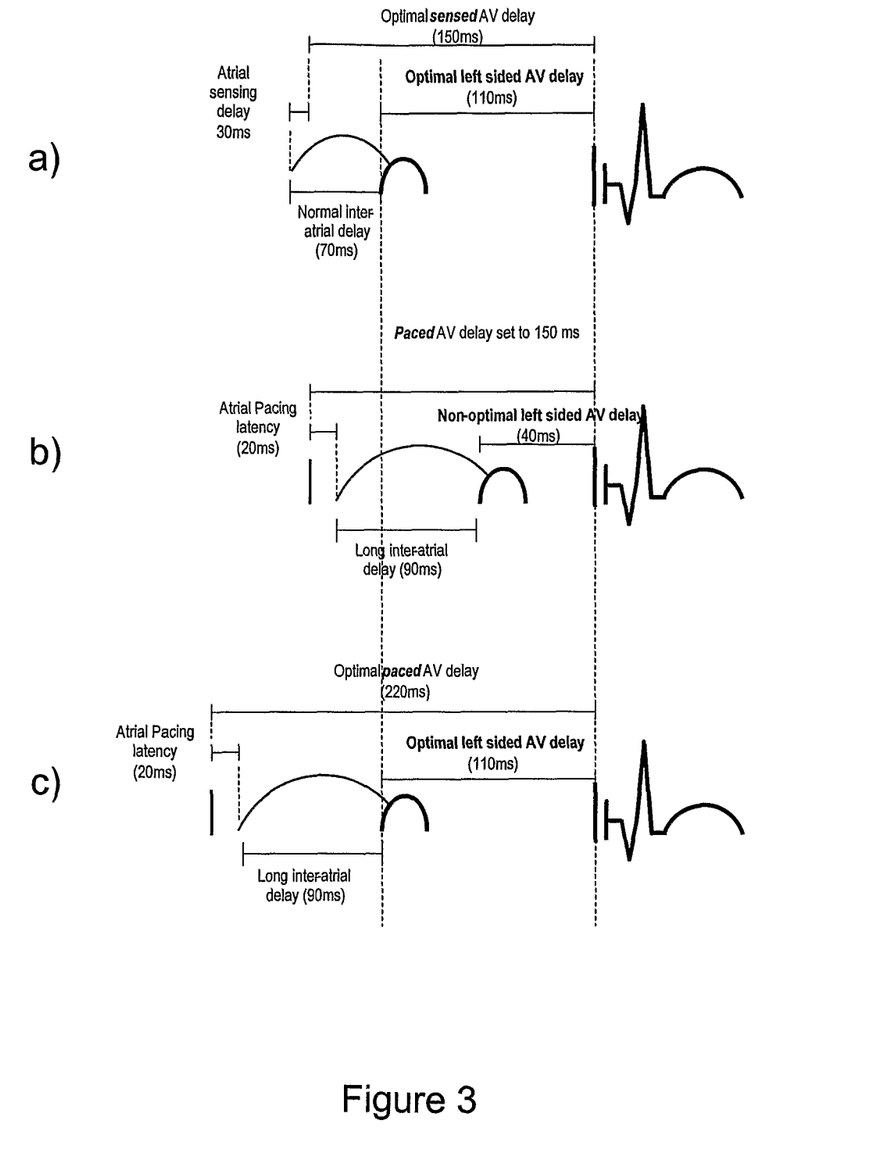
FIG. 3 is a set of stylised graphs showing blood pressure against time for: a) optimal sensed AV delay; b) paced AV delay set to 150 ms; and c) optimal paced AV delay in a hypothetical example.

FIG. 3a shows a graph of blood pressure vs. time of a hypothetical example of an optimal sensed AV delay. The left sided AV delay is likely to be most important in influencing systemic hemodynamics. In this example the left sided AV delay yielding optimal systemic hemodynamics is 110 ms. If this is achieved by atrial sensing, it is necessary to allow for the atrial sensing delay (here 30 ms) and the inter-atrial delay (here 70 ms). This hypothetical patient therefore requires a sensed AV delay of 110+70−30=150 ms.

FIG. 3b shows a corresponding graph but with the paced AV delay programmed to the same value as the sensed AV delay (150 ms in this case). This does not yield the same left sided AV delay. The atrial pacing latency and longer inter-atrial delay mean that sensed and paced AV delays result in different left sided AV delays. If the same AV delay is programmed for the paced AV delay then this results in a non-optimal left sided AV delay (in this example 40 ms). This difference occurs as a result of the atrial pacing latency (here 20 ms) and longer time taken for the atrial signal to travel between the right and left atria manifest as a longer inter-atrial delay (here 90 ms). Here the left sided AV delay is 150−20−90=40 ms.

FIG. 3c shows a corresponding graph wherein, in order to program the same left sided AV delay, as for the optimal sensed AV delay (as shown in FIG. 3a), a longer paced AV delay is programmed (220 ms in this case). That is to say, in order to obtain an optimal left-sided AV delay, the paced AV delay is programmed to a longer value in order to account for the atrial pacing latency and longer inter-atrial delay. This hypothetical patient requires a programmed paced AV delay of 110+90+20=220 ms.

Example 2

Subjects 20 outpatients with biventricular pacemakers or biventricular defibrillators implanted for clinical indications (NYHA III or IV heart failure, QRS>120 ms, maximal medical therapy) were enrolled into the study. Patients were excluded if they were not in sinus rhythm, were pacing dependent or were not able to walk on a treadmill.

Measurements

Data Acquisition

Non-invasive finger arterial pressure measurements were made using a Finometer (Finapres Medical Systems, Amsterdam, Holland). This technique, developed by Peňáz[6] and Wesseling[7] uses a cuff that is placed around the finger, a built-in photo-electric plethysmograph and a volume-clamp circuit that dynamically follows arterial pressure. This technique is well validated for measuring instantaneous changes in blood pressure.[8,9,10,11,12]

An ECG signal was also recorded. These signals were acquired via an analog-to-digital card (National Instruments, Austin, Tex.) using custom developed software[13] and analysed off line with further custom software based on the Matlab platform (MathWorks, Natick, Mass.).

Measurement of Relative Change in Blood Pressure Across Different AV Delays

Beat-to-beat blood pressure was recorded during adjustment of the AV delay of the subjects' biventricular pacemaker. As previously described, the effect of background noise in the blood pressure trace was reduced by calculating the relative change in systolic blood pressure ($SBP_{rel}$). This was done by comparing each transition to a reference AV delay and performing multiple alternations to obtain at least 6 replicate measurements for each $SBP_{rel}$. These were combined to obtain, for each tested delay, a mean $SBP_{rel}$.

$SBP_{rel}$ was measured in the manner described above for a range of AV delays which were 40, 80, 120, 140, 160, 200, 240 ms the sequence was stopped when intrinsic conduction occurred. The interventricular delay was left at 0 ms or as close as the pacemaker allowed.

AV Delay Optimization Sequences

Optimization was initially performed while the patient rested in the sitting position on a couch. At this resting state haemodynamic optimization of AV delay was performed for three different conditions; P-synchronous pacing at resting heart rate, atrial pacing at 5 bpm above the patients resting rate and atrial pacing at a heart rate of 100 bpm. The patient then exercised on a treadmill, workload was adjusted to maintain their heart rate between 100 and 110 bpm, and the P-synchronous AV delay was adjusted.

For each test sequence the AV delay was altered in the above sequence and stopped when intrinsic conduction occurred.

Method for Predicting the Optimal AV Delay During Exercise by Pacing at Rest

Individual patients the optimal AV delay identified during AV delay optimisation differs depending on whether optimisation is performed at rest or during exercise. In order to identify the exercise optimal AV delay at rest, heart rate was increased to the exercise level by atrial pacing and an adjustment was made for the difference between the atrial paced AV delay and the P-synchronous AV delay, the so called 'sensed-paced difference'.

The 'sensed-paced difference' was calculated by determining the difference between the optimal AV delay determined while atrially pacing at 5 bpm above the patients resting heart rate, and that determined during P-synchronous pacing at resting heart rate.

The 'sensed-paced difference' was then subtracted from the optimal AV delay determined while atrially pacing at a heart rate of 100 bpm. This gave us an estimate of optimal AV delay determined during exercise.

To summarise the optimum exercise AV delay was determined using the following equation.

$$\text{Exercise optimal AVD} = \text{optAVD}_{ap100\,bpm} - (\text{optAVD}_{aprr} - \text{optAVD}_{psynchrr})$$

$\text{optAVD}_{ap100\,bpm}$: optimal AVD delay determined while atrially pacing at a rate of 100 bpm.
$\text{optAVD}_{aprr}$: optimal AV delay determined while atrially pacing at a rate 5 bpm above the patients intrinsic rate.
$\text{optAVD}_{psynchrr}$: optimal AV delay determined during P-synchronous pacing at intrinsic rate.

Figure 4:
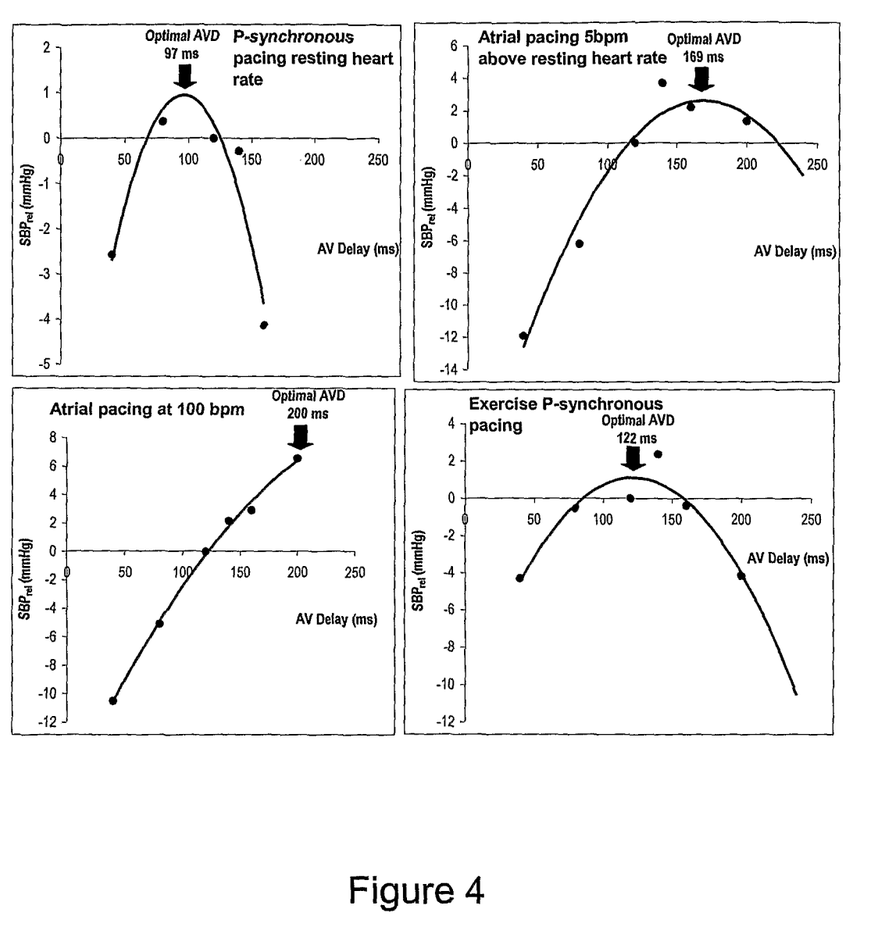
FIG. 4 depicts four graphs providing an example in an individual patient of the method used in the pacing model for predicting exercise optimal AV delay.

FIG. 4 shows an example in an individual patient of graphs of AV delay against blood pressure of the patient undergoing P-synchronous and atrial pacing at resting and raised heart rates. Using the pacing model for predicting exercise optimal AV delay, the calculation is as follows.

$$\text{Predicted } Opt. \ ex \ AVD = 200 - (169 - 97)$$
$$= 128 \text{ ms}$$

As can be seen, the prediction of an optimal exercise AV delay of 128 ms correlates favourably with the measured optimal AV delay of 122 ms.

Statistics

The $\text{SBP}_{rel}$ value was determined for each tested combination of AV and VV delay in relation to a reference AV delay (120 ms) and VV delay (0 ms) by taking the mean of observed blood pressure changes from at least 6 individual transitions. Paired comparisons were made using Student's paired t test. Comparisons of proportions were made using Fisher's exact test. A p value of <0.05 was taken as statistically significant. The statistical package Statview 5.0 (SAS Institute Inc., Cary, N.C.) was used for analysis.

Results

Patient Characteristics

Twenty patients with biventricular pacemakers or biventricular ICD's were enrolled into the study, a mean of 12 months after implantation. 11 were male, 9 female, age range 46-79 years (mean 68.5 years). Cause of heart failure was ischemic in 11, and idiopathic dilated in 9. Mean systolic blood pressure by sphygmomanometer was 116.4+/−18.3 mmHg. Mean ejection fraction of the patients at the time of the study was 30+/−4.9%. 1 patient was in NYHA class I, 13 were in NYHA II, 6 were in NYHA III at the time of the study. Patients gave informed consent for this study which was approved by the local ethical committee.

Parabolic Shape of Haemodynamic Response

Figure 5:
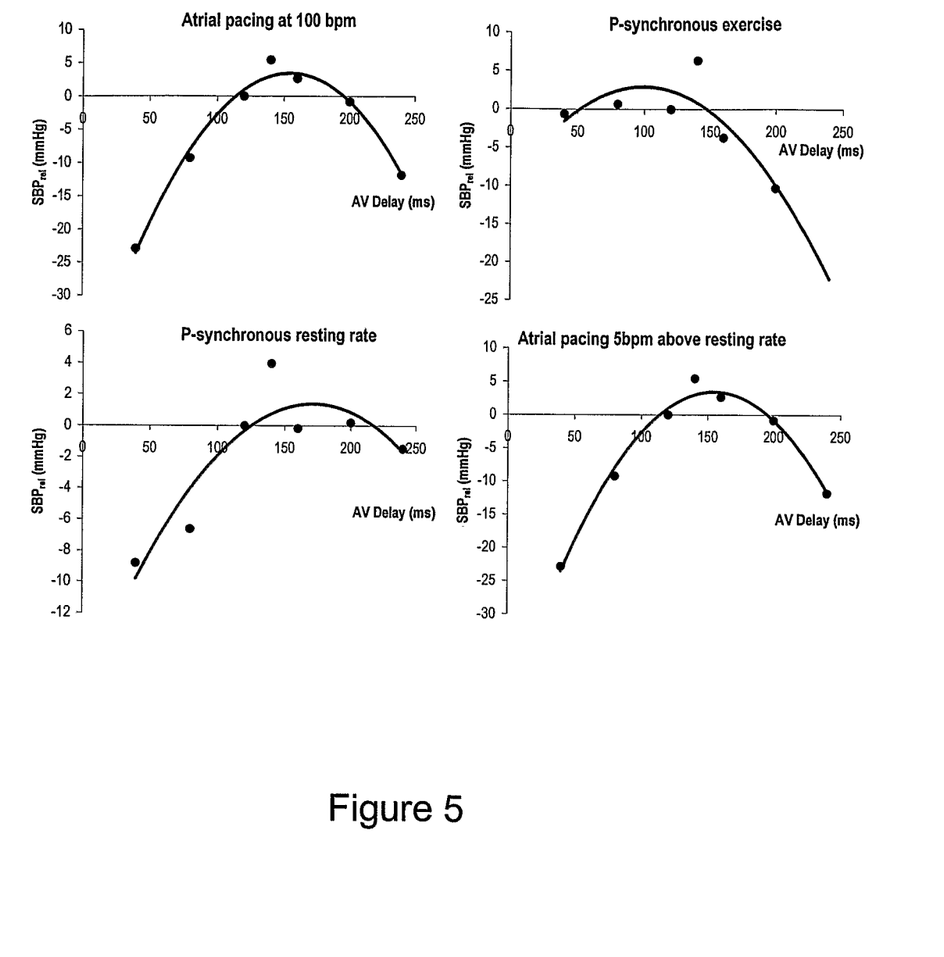
FIG. 5 depicts four graphs providing an example of the haemodynamic response curves obtained in an individual patient.

The effects of changing AV delay were curvilinear rather than linear and fitted closely to a parabola, both at an elevated heart rate and lower heart rate, with atrial pacing or p-synchronous pacing. Therefore it was possible to use parabolic interpolation to identify the peak AV delay for each tested series (FIG. 5). The haemodynamic response curves are shown for optimisation of AV delay during exercise with a heart rate of between 100-110 bpm, during atrial pacing at 100 bpm, P-synchronous pacing at resting rate and atrial pacing at 5 bpm above resting rate.

At resting heart rate with p-synchronous pacing the curve of response to changes in AV delay had a mean $R^2$ for fitting to a parabola of 0.77, the average residual variance away from the parabola was only 0.8 mmHg$^2$. For atrial pacing at 5 bpm above the resting heart rate $R^2$ was 0.9, residual variance 1.7 mmHg$^2$. During exercise with P-synchronous pacing $R^2$ was 0.8 and residual variance was 1.9 mmHg$^2$, while atrially pacing at 100 bpm $R^2$ was 0.9 and residual variance was 4 mmHg$^2$.

Identification of a Haemodynamic Peak

Using continuous non-invasive measurement of blood pressure, it was possible to identify a clear haemodynamic optimal AV delay in all patients, both at rest and with higher heart rates, with atrial pacing and P-synchronous pacing. All patients were able to walk on the treadmill and to raise there heart rate to between 100 and 110 bpm, although in some patients the exercise optimisation needed to be performed in stages in order to allow the patient to rest between different tested AV delays.

The AV delay identified as optimal was specific to the individual patient. The optimal programmed AV delay was on average longer when determined while atrially pacing compared with P-synchronous pacing. This was the case both at lower and higher heart rates. The mean optimal AV delay during atrial pacing at 100 bpm was 183 ms (range 240-140 ms); with P-synchronous pacing during exercise with a heart rate of 100 bpm the mean 125 ms (range 200-80 ms), with atrial pacing at 5 bpm above the resting rate the mean was 182 ms (range 240-140 ms); and with P-synchronous pacing at resting heart rate the mean was 127 ms (range 200-80 ms) (Table 1).

TABLE 1

The AV delay identified as optimal for each individual patient for each of the four different pacing situations

| | Quadratic interpolated optimum AVD (ms) | | | | | Difference | Difference |
|---|---|---|---|---|---|---|---|
| | Rate ~100 | | Rate rest | | | | |
| | Exercise (P-synch) | Atrial Pacing | Sensed (P-synch) | Atrial Pacing | Predicted ex optimum | Exercise & predicted | Exercise & P-synch rest |
| Pt1 | 200 | 200 | 163 | 160 | 203 | 3 | 38 |
| Pt2 | 122 | 162 | 104 | 160 | 106 | 16 | 18 |
| Pt3 | 135 | 160 | 120 | 140 | 140 | 5 | 15 |
| Pt4 | 147 | 213 | 133 | 200 | 146 | 1 | 14 |

TABLE 1-continued

The AV delay identified as optimal for each individual patient for each of the four different pacing situations
Quadratic interpolated optimum AVD (ms)

| | Rate ~100 | | Rate rest | | Difference | Difference |
|---|---|---|---|---|---|---|
| | Exercise (P-synch) | Atrial Pacing | Sensed (P-synch) | Atrial Pacing | Predicted ex optimum | Exercise & predicted | Exercise & P-synch rest |
| Pt5 | 200 | 200 | 200 | 200 | 200 | 0 | 0 |
| Pt6 | 80 | 150 | 80 | 168 | 62 | 18 | 0 |
| Pt7 | 138 | 240 | 120 | 240 | 120 | 18 | 18 |
| Pt9 | 90 | 164 | 82 | 160 | 86 | 4 | 8 |
| Pt10 | 158 | 193 | 140 | 171 | 162 | 4 | 18 |
| Pt11 | 80 | 164 | 109 | 157 | 116 | 36 | 29 |
| Pt12 | 93 | 140 | 120 | 155 | 105 | 12 | 27 |
| Pt13 | 120 | 189 | 134 | 200 | 123 | 3 | 14 |
| Pt14 | 133 | 181 | 134 | 177 | 138 | 5 | 1 |
| Pt15 | 107 | 192 | 111 | 200 | 103 | 4 | 4 |
| Pt16 | 115 | 140 | 140 | 160 | 120 | 5 | 25 |
| Pt17 | 86 | 180 | 118 | 200 | 98 | 12 | 32 |
| Pt18 | 123 | 209 | 156 | 240 | 125 | 3 | 34 |
| Pt19 | 122 | 200 | 97 | 169 | 128 | 6 | 26 |
| Pt20 | 160 | 200 | 160 | 200 | 160 | 0 | 0 |
| mean | 125 | 183 | 127 | 182 | 128 | 8 | 17 |
| SD | 35 | 27 | 29 | 28 | 35 | 9 | 12 |

The AV delay identified as optimal using quadratic interpolation for each of the individual patients is shown for optimization during exercise with a heart rate of 100-110 bpm, optimization while atrially pacing at 100 bpm, optimization during P-synchronous pacing at resting heart rate and optimization while atrially pacing 5 bpm above resting heart rate. The predicted optimal exercise AV delay (Exercise optimal AVD=optAVD$_{ap100\ bpm}$−(optAVD$_{aprr}$−optAVD$_{psynchrr}$)) is shown and the difference between actual exercise and predicted is shown, as is the difference between P-synchronous optimisation at rest and exercise. The mean and standard deviations are shown.

Comparison of Pacing Model and Exercise

While the mean values for the optimal AV delays identified for both the pacing model and P-synchronous pacing at rest do not differ significantly from that identified during exercise, within individual patients the pacing model shows a closer correlation.

The resting pacing model correlated well with the optimal AV delay identified during exercise, $R^2$=0.88, standard deviation of the difference 12.2 ms. Whereas the optimal AV delay identified at rest with P-synchronous pacing shows a poorer correlation with exercise $R^2$ 0.57, SD of the difference 12 ms.

Figure 6:
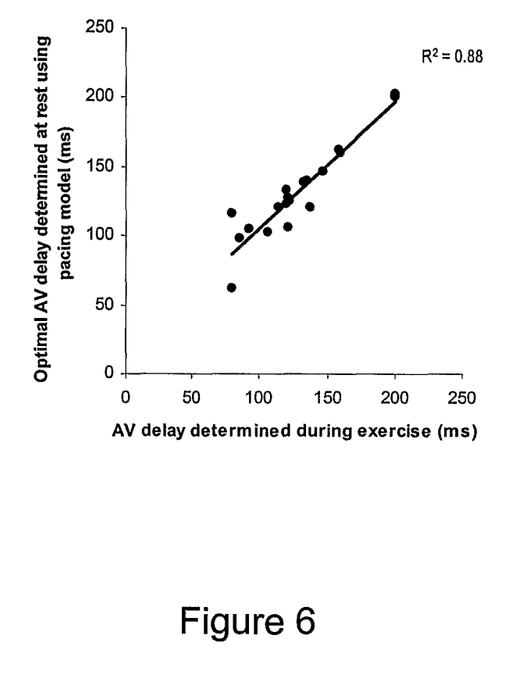
FIG. 6 is a graph showing a comparison of the optimal AV delay identified during exercise and the predicted exercise optimum using the pacing model at rest.

A comparison between the optimal AV delay identified during exercise and the predicted exercise optimum using the pacing model at rest is shown in FIG. 6. There is a strong correlation between the actual optimal AV delay determined by performing optimisation during exercise and the predicted optimal AV delay determined using the resting pacing model. This means it is possible to predict the optimal exercise AV delay without exercising the patient.

Haemodynamic Consequence of Using Pacing Model and P-Synchronous Pacing at Rest to Select Programmed AV Delay In order to assess the haemodynamic consequence during exercise, of using either the pacing model or P-synchronous pacing at rest to select the programmed AV delay, the change in SBP$_{rel}$ was calculated from the actual exercise optimum for each individual patient's exercise haemodynamic parabola.

There was a mean 0.2 mmHg (±0.5 mmHg) difference in SBP$_{rel}$ when using the resting pacing model to select the exercise optimal AV delay compared with the actual AV delay identified during exercise (p=NS), whereas there was a 1.1 mmHg (±2.2 mmHg) fall in SBP$_{rel}$ when selecting the peak AV delay by performing optimisation at resting heart rate with P-synchronous pacing (p=0.046).

Discussion

This study demonstrates a method for optimization of the AV delay of CRT devices which allows optimization to be performed during exercise. Secondly, the study shows that the haemodynamic response to changes in AV delay is curvilinear rather than linear and fits closely to a parabola both at lower heart and elevated heart rates. Thirdly, the study shows that optimisation at resting heart rates with P-synchronous pacing selects an AV delay which correlates reasonably well with the exercise optimum. Fourthly, the study shows that correlation with exercise can be improved substantially by using a pacing model for exercise at rest. Finally by using this pacing model patients gain significant haemodynamic improvements over standard optimization with P-synchronous pacing at resting heart rates.

Haemodynamic Consequence of Using Pacing Model or P-Synchronous Optimization at Rest when Selecting the AV Delay During Exercise A difference of 0.9 mmHg in acute blood pressure change represents a substantial difference in cardiac function.

The onset of biventricular pacing resulted in a mean increase in acute aortic systolic pulse pressure of 2 mmHg in a previous invasive study. This is consistent with the landmark trials with cardiac resynchronisation therapy which showed an increase in blood pressure, paralleling the improvements in symptoms and survival, for patients entered into the device arm. For example in the COMPANION trial, patients in the resynchronisation arm initially gained approximately 2 mmHg (confidence interval not published) in systolic blood pressure (in comparison to the control arm) and went on to have a 18% relative reduction (95% confidence interval 1% increase to 42% reduction) in the combined endpoint of morbidity and mortality.[14] Similarly the Care-HF trial showed, at three months, that the increment in blood pressure attributable to being in the device arm was 5.8 (95% CI 3.5 to 8.2) mmHg, and the mortality reduction was 37 (95% CI: 23 to 49) percent.[15]

Cross-sectional observational data suggest a 4% (95% confidence interval 3% to 5%) relative increase in mortality per mmHg decline in systolic blood pressure in outpatients with chronic heart failure.[16]

This shows that patients gain important additional benefit from their cardiac resynchronization devices if their AV delay optimization is tailored to provide the best possible AV delay for when they exercise (the time most patients become symptomatic).

CONCLUSIONS

Using acute non-invasive haemodynamics to calculate mean relative change in blood pressure, it is possible to optimize the AV delay of cardiac resynchronization devices whilst a patient exercises. Optimization at resting heart rate during P-synchronous pacing correlates with the optimum identified during exercise. However, using a resting pacing model this correlation can be substantially improved which has significant acute haemodynamic benefits for individual patients.

REFERENCE

[1] Cha Y M, Nishimura R A, Hayes D L. Differences in mechanical atrioventricular delay between atrial sensing and atrial pacing modes in patients with hypertrophic and dilated cardoimyopathy: An electrical hemodynamic catheterization study. *J Interv Card Electrophysiol* 2002; 6:133-140.

[2] Wish M, Fletcher R D, Gottdiener J R, Cohen A I. Importance of left atrial timing in the programming of dual-chamber pacemakers. *Am J Cardiol* 1987; 60:566-571.

[3] Janosik D L, Pearson A C, Buckingham T A, Labovitz A J, Redd R M. The hemodynamic benefit of differential atrioventricular delay intervals for sensed and paced atrial events during physiologic pacing. *J Am Coll Cardiol* 1989; 14:499-507.

[4] Catonia S L, Maue-Dickson W. AV Delay Latency Compensation. *J Electrophysiology* 1987; 1:242-249.

[5] Ausubel K, Klementowicz P, Furman S. Interatrial Conduction During Cardiac pacing. *PACE*. 1986; 9:1026-1031.

Peñáz[6] J Photoelectric measurement of blood pressure, volume and flow in the finger. Digest of the international Conference on Medicine and Biological Engineering, Dresden, 1973 p 104 [abstract].

[7] Wessling K H, De Wit B, Van der Hoeven G M, Van Goudover J and Settels J. Physiocal calibrating finger vascular physiology for Finapres. *Homeostasis* 1995; 36:67-82.

[8] Smith N T, Wesseling K H, deWit B. Evaluation of two prototype devices producing non-invasive, pulsatile, calibrated blood pressure measurement from a finger. *J Clin Monitoring*. 1985:1; 17-29.

[9] Van Egmond J, Hasenbos M, Crul J F: Invasive versus. non-invasive measurement of arterial pressure. Comparison of two automatic methods and simultaneously measures direct intraarterial pressure. *Br J Anaesth* 1985; 57:434-444.

[10] Petersen M E, Williams T R, Sutton R. A comparison of non-invasive continuous finger blood pressure measurement (Finapres) with intra-arterial pressure during prolonged head-up tilt. *Eur Heart Journal* 1995; 16:1647-1654.

[11] Jellema W T, Imholz P M, van Goudoever J, Wesseling K H, van Lieshout J. Finger arterial versus intrabrachial pressure and continuous cardiac output during head-up tilt testing in healthy subjects. *Clin Sci* 1996; 91:193-200.

[12] Imholz B P M, Welling W, Montfrans G A, Wesseling K H. Fifteen years experience with finger arterial pressure monitoring: assessment of the technology. *Cardiovasc. Res.* 1998; 38: 605-616.

[13] Davies L C, Francis D P, Jurak P, Kara T, Piepoli M, Coats A J S. Reproducibility of methods for assessing baroreflex sensitivity in normal controls and in patients with chronic heart failure. *Clin Sci(Lond)* 1999; 97:515-522.

[14] Bristow M R, Saxon L A, Boehmer J, Krueger S, Kass D A, De Marco T, Carson P, Di Carlo L, DeMets D, White B G, DeVries D W, Feldman A M. Cardiac-resynchronization Therapy with or without an implantable Defibrillator in Advanced Chronic Heart Failure. *N Engl J Med.* 2004; 350:2140-50.

[15] Cleland J G, Daubert J C, Erdmann E, Freemantle N, Gras D, Kappenberger L, Tavazzi L. The Effect of Cardiac Resynchronization on Morbidity and Mortality in Heart Failure. *N Engl J Med* 2005; 352(15):1539-49.

[16] Shamim W, Francis D P, Yousufuddin M, Varney S, Pieopli M F, Anker S D, Coats A J. Intraventricular conduction delay: a prognostic marker in chronic heart failure. *Int J Cardiol.* 1999; 70:171-78.

The invention claimed is:

1. A pacemaker programming apparatus for programming a pacemaker in an individual comprising:
   a monitoring device, configured to determine a haemodynamic measure of the individual;
   a processor, configured to:
   i) set the pacemaker to P-synchronous pacing at a specific heart rate and adjust an AV delay of the pacemaker to determine the optimum AV delay based on the haemodynamic measure of the individual;
   ii) switch the pacemaker to atrial pacing at or near the specific heart rate and adjust the AV delay of the pacemaker to determine the optimum AV delay based on the haemodynamic measure of the individual;
   iii) determine the sensed-paced difference of the pacemaker in the individual by deducting the optimum AV delay determined in step i) from the optimum AV delay determined in step ii);
   iv) adjust the pacemaker to atrially pace at a raised heart rate and adjust the AV delay of the pacemaker to determine the optimum AV delay based on the haemodynamic measure of the individual; and
   v) calculate the optimum AV delay determined in step iv) minus the sensed-paced difference determined in step iii).

2. The pacemaker programming apparatus according to claim 1 further comprising means to communicate with the pacemaker in the individual.

3. The pacemaker programming apparatus according to claim 1 wherein the raised heart rate is between 90 and 200 bpm.

4. The pacemaker programming apparatus according to claim 3 wherein the raised heart rate is between 95 and 110 bpm.

5. The pacemaker programming apparatus according to claim 1 wherein the optimum AV delay of a pacemaker is the AV delay which provides the highest blood pressure in an individual.

6. The pacemaker programming apparatus according to claim 1 wherein determining the optimum AV delay comprises varying the AV delay whilst measuring the blood pressure of the individual and determining the AV delay which results in the highest blood pressure of the individual.

7. The pacemaker programming apparatus according to claim 6 wherein the optimum AV delay is determined by alternating the AV delay of the pacemaker between a reference AV delay and a range of test AV delays to determine the test AV delay which provides the maximum relative increase in blood pressure in the individual.

8. The pacemaker programming apparatus according to claim 1 wherein the specific heart rate is a rest heart rate.

9. The pacemaker programming apparatus according to claim 8 wherein the rest heart rate is between 60 and 100 bpm.

10. The pacemaker programming apparatus according to claim 9 wherein the rest heart rate is between 65 and 80 bpm.

11. The pacemaker programming apparatus according to claim 1 wherein a heart rate near the specific heart rate is within a rate selected from the group consisting of 10, 15 and 20 bpm of the specific heart rate.

12. The pacemaker programming apparatus according to claim 1 wherein a heart rate near the specific heart rate is within 5 bpm of the specific heart rate.

13. The pacemaker programming apparatus according to claim 1, wherein the processor is configured to execute a non-transitory program storage medium having a computer program stored thereon for performing the steps of:
  determining the haemodynamic measure of the individual;
  setting the pacemaker to P-synchronous pacing at the specific heart rate and adjusting the AV delay of the pacemaker to determine the optimum AV delay based on the haemodynamic measure of the individual;
  switching the pacemaker to atrial pacing at or near the specific heart rate and adjusting the AV delay of the pacemaker to determine the optimum AV delay based on the haemodynamic measure of the individual;
  determining the sensed-paced difference of the pacemaker in the individual by deducting the optimum AV delay determined in step i) from the optimum AV delay determined in step ii);
  adjusting the pacemaker to atrially pace at the raised heart rate and adjusting the AV delay of the pacemaker to determine the optimum AV delay based on the haemodynamic measure of the individual; and
  calculating the optimum AV delay determined in step iv) minus the sensed-paced difference determined in step iii).

14. A non-transitory program storage medium storing a computer program, which when executed by a pacemaker programming apparatus, performs the steps of:
  i) determining a haemodynamic measure of an individual;
  ii) setting a pacemaker to P-synchronous pacing at a specific heart rate and adjusting an AV delay of the pacemaker to determine the optimum AV delay based on the haemodynamic measure of the individual;
  iii) switching the pacemaker to atrial pacing at or near the specific heart rate and adjusting the AV delay of the pacemaker to determine the optimum AV delay based on the haemodynamic measure of the individual;
  iv) determining the sensed-paced difference of the pacemaker in the individual by deducting the optimum AV delay determined in step ii) from the optimum AV delay determined in step iii);
  v) adjusting the pacemaker to atrially pace at a raised heart rate and adjusting the AV delay of the pacemaker to determine the optimum AV delay based on the haemodynamic measure of the individual; and
  vi) calculating the optimum AV delay determined in step v) minus the sensed-paced difference determined in step iv).

15. The non-transitory program storage medium according to claim 14 wherein the raised heart rate is between 90 and 200 bpm.

16. The non-transitory program storage medium according to claim 15 wherein the raised heart rate is between 95 and 110 bpm.

17. The non-transitory program storage medium according to claim 14 wherein the optimum AV delay of a pacemaker is the AV delay which provides the highest blood pressure in an individual.

18. The non-transitory program storage medium according to claim 14 wherein determining the optimum AV delay comprises varying the AV delay whilst measuring the blood pressure of the individual and determining the AV delay which results in the highest blood pressure of the individual.

19. The non-transitory program storage medium according to claim 18 wherein the optimum AV delay is determined by alternating the AV delay of the pacemaker between a reference AV delay and a range of test AV delays to determine the test AV delay which provides the maximum relative increase in blood pressure in the individual.

20. The non-transitory program storage medium according to claim 14 wherein the specific heart rate is a rest heart rate.

21. The non-transitory program storage medium according to claim 20 wherein the rest heart rate is between 60 and 100 bpm.

22. The non-transitory program storage medium according to claim 21 wherein the rest heart rate is between 65 and 80 bpm.

23. The non-transitory program storage medium according to claim 14 wherein a heart rate near the specific heart rate is within a rate selected from the group consisting of 10, 15 and 20 bpm of the specific heart rate.

24. The non-transitory program storage medium according to claim 14 wherein a heart rate near the specific heart rate is within 5 bpm of the specific heart rate.

25. A non-transitory program storage medium storing a computer program, which when executed by a pacemaker programming apparatus, performs the steps of:
  i) determining the sensed-paced difference of the pacemaker in the individual, by:
    a) determining optimum AV delay while the pacemaker is P-synchronous pacing at a specific heart rate,
    b) determining optimum AV delay while the pacemaker is atrially pacing at or near the specific heart rate, and
    c) determining the difference between the optimum AV delay determined at step a) and the optimum AV delay determined at step b);
  ii) determining optimum AV delay while the pacemaker is atrially pacing at a raised heart rate; and
  iii) adjusting the optimum AV delay determined at step ii) with the sensed-paced difference determined at step i), by calculating the optimum AV delay determined at the raised heart rate minus the optimum AV delay determined while atrially pacing at or near the specific heart rate plus the optimum AV delay determined while P-synchronous pacing at the specific heart rate.

26. The non-transitory program storage medium according to claim 25 wherein the optimum AV delay of a pacemaker is the AV delay which provides the highest blood pressure in an individual.

27. The non-transitory program storage medium according to claim 25 wherein determining the optimum AV delay comprises varying the AV delay whilst measuring the blood pressure of the individual and determining the AV delay which results in the highest blood pressure of the individual.

28. The method according to claim 27 wherein the optimum AV delay is determined by alternating the AV delay of the pacemaker between a reference AV delay and a range of test AV delays to determine the test AV delay which provides the maximum relative increase in blood pressure in the individual.

29. The non-transitory program storage medium according to claim 25 wherein the specific heart rate is a rest heart rate.

30. The non-transitory program storage medium according to claim 29 wherein the rest heart rate is between 60 and 100 bpm.

31. The non-transitory program storage medium according to claim 30 wherein the rest heart rate is between 65 and 80 bpm.

32. The non-transitory program storage medium according to claim 25 wherein a heart rate near the specific heart rate is within a rate selected from the group consisting of 10, 15 and 20 bpm of the specific heart rate.

33. The non-transitory program storage medium according to claim 32 wherein a heart rate near the specific heart rate is within 5 bpm of the specific heart rate.

34. The non-transitory program storage medium according to claim 25 wherein step iii) comprises deducting the optimum AV delay determined at step i) from the optimum AV delay determined at step ii).

35. A method of determining a preferred AV delay for a pacemaker in an individual comprising:
  i) determining the sensed-paced difference of the pacemaker in the individual, by:
    a) determining optimum AV delay while the pacemaker is P-synchronous pacing at a specific heart rate,
    b) determining optimum AV delay while the pacemaker is atrially pacing at or near the specific heart rate, and
    c) determining the difference between the optimum AV delay determined at step a) and the optimum AV delay determined at step b);
  ii) determining optimum AV delay while the pacemaker is atrially pacing at a raised heart rate; and
  iii) adjusting the optimum AV delay determined at step ii) with the sensed-paced difference determined at step i), by calculating the optimum AV delay determined at a raised heart rate minus the optimum AV delay determined while atrially pacing at or near the specific heart rate plus the optimum AV delay determined while P-synchronous pacing at the specific heart rate.

36. The method according to claim 35 wherein the raised heart rate is between 90 and 200 bpm.

37. The method according to claim 36 wherein the raised heart rate is between 95 and 110 bpm.

38. The method of programming a pacemaker in an individual comprising carrying out the method of claim 35 and further comprising the step of iv) programming the pacemaker with the AV delay determined at step iii).

* * * * *